United States Patent [19]

Carr

[11] 4,102,912

[45] Jul. 25, 1978

[54] PROCESS TO PREPARE POLYHALODIPHENYL CARBONATES

[75] Inventor: Dennis James Carr, Mt. Vernon, Ind.

[73] Assignee: General Electric Company, Pittsfield, Mass.

[21] Appl. No.: 768,179

[22] Filed: Feb. 14, 1977

[51] Int. Cl.² .......................................... C07C 68/02
[52] U.S. Cl. .................................................. 260/463
[58] Field of Search ........................................ 260/463

[56] References Cited

U.S. PATENT DOCUMENTS

| 3,017,424 | 1/1962 | Meyer et al. | 260/463 |
| 3,275,674 | 9/1966 | Bottenbruch et al. | 260/463 |
| 4,016,190 | 4/1977 | Böckmann et al. | 260/463 |

FOREIGN PATENT DOCUMENTS

| 647,546 | 8/1962 | Canada | 260/463 |

Primary Examiner—Lewis Gotts
Assistant Examiner—Molly C. Eakin
Attorney, Agent, or Firm—Salvatore C. Mitri; William F. Mufatti

[57] ABSTRACT

An improvement in the process of preparing a polyhalodiphenyl carbonate containing 6–10 halogen atoms from a reaction in a basic aqueous medium of a polyhalophenol and a carbonate precursor in the presence of a suitable catalyst, the improvement comprising reacting the components at a pH above about 10.5 in the presence of a solvent in which the polyhalodiphenyl carbonate is essentially insoluble and in which color bodies associated with polyhalophenol are soluble and retained. The improved process produces a polyhalodiphenyl carbonate which is essentially colorless and which possesses a low residual chloride content.

5 Claims, No Drawings

PROCESS TO PREPARE POLYHALODIPHENYL CARBONATES

This invention is directed to an improved process to prepare a polyhalodiphenyl carbonate containing 6-10 halogen atoms wherein in said improved process the reactants are reactd at a pH above about 10.5 and in the presence of a solvent in which the polyhalodiphenyl carbonate is essentially insoluble and in which color bodies associated with polyhalophenol are soluble and retained.

BACKGROUND OF THE INVENTION

Inclusion of a polyhalodiphenyl carbonate containing 6-10 halogen atoms as a component of a polymer composition imparts flame retardant qualities to the composition. Such flame retardant characteristics are shown in U.S. Pat. No. 3,382,207, which describes a flame retardant high ignition temperature polymer composition comprising in admixture a thermoplastic polymer and at least 1.0 weight percent of a polyhalodiphenyl carbonate containing 6-10 halogen atoms.

In order to retain favorable color and low residual chloride content characteristics of the particular polymer composition, it is necessary to provide for subsequent blending with the polymer a polyhalodiphenyl carbonate which is essentially colorless and low in chloride content. One method of preparation of the polyhalodiphenyl carbonate is to react a polyhalophenol such as pentabromophenol with a carbonate precursor such as carbonyl chloride in a reaction medium which is either a tertiary amine organic solvent medium or an aqueous medium which includes a tertiary amine or other suitable compound as a catalyst for the reaction. In the aqueous medium, the pH is about 9.5 - 10.5. However, the polyhalodiphenyl carbonate so produced must be further purified as through recrystallization in order to be an acceptable component of many polymer compositions. Initial unacceptability of said polyhalodiphenyl carbonate is due to a relatively high residual chloride content which can be detrimental to the physical properties of the polymer with which the polyhalodiphenyl carbonate is to be blended. Further, color bodies which can be isomers and unknown impurities associated with the polyhalophenol starting material remain with the polyhalodiphenyl carbonate. If these color bodies are not compatible with the color desired to the end-product polymer, they, likewise, must be removed as through a recrystallization purification process.

SUMMARY OF THE INVENTION

It has now been surprisingly discovered that reacting the reactants employed in producing a polyhalodiphenyl carbonate at a pH above about 10.5 in the presence of a solvent in which the polyhalodiphenyl carbonate is essentially insoluble and in which color bodies associated with polyhalophenol are soluble and retained produces a polyhalodiphenyl carbonate which is essentially colorless and which possesses a low residual chloride content without requiring further purification.

The polyhalophenol used as a starting reactant can be chosen from those commonly known in the art, representative, but not limiting, compounds being pentabromophenol, pentachlorophenol, tetrafluorophenol, tribromophenol, triiodophenol, and the like, or mixtures thereof.

Carbonate precursors which can be employed include a carbonyl halide or a haloformate. The carbonyl halides include carbonyl bromide, carbonyl chloride, carbonyl fluoride, or mixtures thereof. The haloformates include bishaloformates or dihydric phenols such as bischloroformates of hydroquinone and the like; or bishaloformates of glycols such as bishaloformates of ethylene glycol, neopentyl glycol, polyethylene glycol, and the like. Monohaloformates include phenylchloroformate, tribromophenylchloroformate, and the like. While other carbonate precursors will occur to those skilled in the art, carbonyl chloride, also known as phosgene, is preferred.

Upon reaction of a respective polyhalophenol with a respective carbonate precursor, the following representative polyhalodiphenyl carbonates can be produced: hexabromodiphenyl carbonate, decabromodiphenyl carbonate, hexachlorodiphenyl carbonate, decachlorodiphenyl carbonate, hexafluorodiphenyl carbonate, pentabromopentachlorodiphenyl carbonate, and the like, and mixtures thereof. One preferred polyhalodiphenyl carbonate for use as a flame retardant in a polycarbonate polymer flame retardant composition is decabromodiphenyl carbonate.

As earlier related, the reaction of the polyhalophenol and the carbonate precursor is accomplished at a pH above about 10.5, with a preferred pH range being about 10.5 - 11.5. The pH value is achieved and maintained by the addition of a base such as an alkali metal hydroxide or alkaline earth metal hydroxide to the reaction mix. The preferred base is sodium hydroxide.

The reaction is carried out in the presence of a catalyst which promotes reaction of the polyhalophenol and carbonate precursor. Said reaction can be carried out at ambient temperature and pressure. Catalysts which can be used are tertiary amines such as trimethyl amine, triethyl amine, tripropyl amine, tributyl amine, methyl ethyl amine, dimethyl ethyl amine, quinoline, isoquinoline, etc., or mixtures thereof; quaternary ammonium salts such as tetramethyl ammonium chloride, trimethyl ammonium propyl iodide, benzyl trimethyl ammonium iodide, etc., or mixtures thereof; or quaternary phosphonium compounds such as n-butyl-triphenyl phosphonium bromide and methyl-triphenyl phosphonium bromide, or mixtures thereof. Also, mixtures of these various catalysts are within the scope of this invention. A preferred catalyst is triethyl amine present in an amount of about 2.5 weight percent of the polyhalophenol reactant.

Solvent present in the reaction mix acts to retain color bodies associated with polyhalophenols. The polyhalodiphenyl carbonate product produced in the reaction must be essentially insoluble in the solvent, however, so that said product can be physically separated from the mix. The temperature of the reaction mix must be below the boiling point of the solvent so that said solvent remains in the liquid state. A preferred method of assuring maintenance of such a temperature is utilization of a reflux condenser which cools and re-liquifies any vaporized solvent for return to and consequent cooling of the reaction mix. Alternatively or additionally, temperature and pressure conditions can be externally controlled to keep the solvent in the liquid state. Solvents which can be used are chlorinated hydrocarbons such as methylene chloride, ethylene dichloride, chloroform, carbon tetrachloride, trichloroethylene, etc., or mixtures thereof. A preferred solvent is methylene chloride. Solvent retention of the color bodies referred to above thus assists in the production of an essentially colorless polyhalodiphenyl carbonate product.

In addition to being essentially colorless, the polyhalodiphenyl carbonate product produced according to this invention possesses an acceptably low residual chloride content. Thus, the product can be metered without recrystallization purification to a polymer composition for subsequent high temperature molding.

DESCRIPTION OF PREFERRED EMBODIMENTS

The following examples are set forth to illustrate more clearly the principle and practice of this invention to those skilled in the art. Unless otherwise specified, where parts or percents are mentioned, they are parts or percents by weight.

EXAMPLE I

A 5,000 ml round bottom flask equipped with a stirrer, condenser, dip tube, pH electrode, and addition funnel is charged with 733 grams pentabromophenol, 2,500 ml methylene chloride, 1,000 ml water, and 25 ml triethylamine. To this mixture is added sufficient 50% sodium hydroxide solution to reach a pH of about 11. Continuous carbonyl chloride addition is then begun at a rate of 2.1 grams per minute during the reaction time for a total of 85.1 grams, and further addition of the 50% sodium hydroxide solution is performed to maintain the pH of the reaction at about 11. Actual pH range during the course of the reaction is 10.9 – 11.6. Continuous carbonyl chloride addition is accomplished through use of a Tri-Flat Variable-Area Flow Meter manufactured by Fischer-Porter Co. Of course, other rate-control means can be employed as known in the art. External heat is not applied, and, over the 40 minute course of the reaction, the temperature rises from 28° C to 38° C. At the end of the 40-minute reaction period, carbonyl chloride addition is discontinued while stirring continues for about 10 minutes. During this time, the pH value drops and additional sodium hydroxide is added, yielding a pH of 9.2 at the end of the procedure.

The entire reaction mix is then filtered through a sintered glass funnel and the precipitate is washed with water in a Waring blender until the pH is neutral to litmus paper. The precipitate is then washed once with methanol to remove excess water, again filtered through a sintered glass funnel, and finally air dried. The melting point of the product, decabromodiphenyl carbonate, is found to be 358° C. Said product is then further dried, first, in a vacuum oven at 150° C for 2 hours, and second, in an air-circulating oven at 125° C for 2 hours. Weight of the final product is 712 grams, a yield of 94.6% of the theoretical yield. Chloride content in the final product is 253 parts per million, and the product is essentially colorless.

Further reduction as required of chloride content can be accomplished through further washing of the product. Thus, for example, the above product can be washed four times with water, twice with methanol, and once with methylene chloride. After air drying and further heat drying in an air-circulating oven for 1 hour at 125° C, the product so treated yields 697.3 grams of product representing a yield of 92.7% of the theoretical yield. Chloride content is found to be 114 parts per million.

EXAMPLE II

A 2,000 ml round bottom flask equipped with a stirrer, condenser, dip tube, pH electrode, and addition funnel is charged with 97.7 grams pentabromophenol, 450 ml methylene chloride, 240 ml water, and 3.5 ml triethylamine. To this mixture is added sufficient 25% sodium hydroxide solution to reach a pH of 11.5. Continuous carbonyl chloride addition is then begun at a rate of 0.58 grams per minute during the reaction time for a total of 11.4 grams, and further addition of the 25% sodium hydroxide solution is performed to maintain the pH of the reaction at about 11. The pH is maintained until the entire reaction is completed, and no pH drop occurs during final stirring.

The entire reaction mix is then filtered through a sintered glass funnel and repeatedly washed with water until the pH is neutral to litmus paper. The precipitate is then washed once with methanol to remove excess water, then washed with methylene chloride, and finally air dried. The melting point of the product, decabromodiphenyl carbonate, is 354° C. Yield is 92.7 grams, 92.4% of the theoretical yield. Chloride content is 31 parts per million, and the product requires no further washing and recrystallization.

EXAMPLE III

This example is included to compare results obtained when the pH is maintained about 10.5 but when no methylene chloride is employed.

In the same manner as in Example II, 97.7 grams pentabromophenol, 700 ml water, and 3.5 ml triethylamine are charged to the 2,000 ml round bottom flask equipped as in Example II. The starting pH is 11.2, and is maintained throughout the reaction at 10.5 – 11.2. Continuous carbonyl chloride addition is performed at a rate of 0.58 grams per minute for a total of 11.4 grams. Upon completion of the reaction, filtration of product was attempted, but was impossible to perform. The reaction mixture is allowed to settle and a portion of the settled precipitate is found to have a sticky nature and to be very impure. Analysis of product cannot be performed.

EXAMPLE IV

This example is included to compare results obtained when the pH is maintained below 10.5 and methylene chloride is employed.

In the same manner as in Example II, 97.7 grams pentabromophenol, 450 ml methylene chloride, 240 ml water, and 3.5 ml triethylamine are charged to the 2,00 ml round bottom flask equipped as in Example II. The starting pH is 9.6, and is maintained throughout the reaction at 9.4 – 9.8. Continuous carbonyl chloride addition is performed at a rate of 0.58 grams per minute for a total of 11.4 grams. Upon completion of the reaction, the entire reaction mix is filtered through a sintered glass funnel. Said filtration is considerably slower than that found in Examples I and II. After filtration, the product is repeatedly washed with water until the pH is neutral to litmus paper. The precipitate is then washed with methanol and methylene chloride as in Example II, and air dried. The melting point of the product, decabromodiphenyl carbonate, is 351°–352° C. Chloride content is 81 parts per million, and yield is 79.9 grams, only 79.7% of the theoretical yield.

Thus, maintenance of a high pH and utilization of a solvent in which the polyhalodiphenyl carbonate is essentially insoluble but in which color bodies associated with polyhalophenol are retained provides a process for high purity and high yield production of polyhalodiphenyl carbonate.

Obviously, other modifications and variations of the present invention are possible in light of the above teachings. It is, therefore, to be understood that changes may be made in the particular embodiments of the invention described which are within the full intended scope of the invention as defined by the appended claims.

What is claimed is:

1. In a method of preparing a polyhalodiphenyl carbonate containing 6 to 10 halogen atoms by reacting a polyhalophenol and a carbonate precursor in the presence of a catalyst in a basic aqueous medium, the improvement comprising carrying out the reaction in a continuous, single stage at a pH in the range of about 10.5 to 11.5 and in the presence of a chlorinated hydrocarbon solvent in which the polyhalodiphenyl carbonate is essentially insoluble and in which color bodies associated with the polyhalophenol starting material are soluble and retained.

2. In a method of preparing a polyhalodiphenyl carbonate containing 6 to 10 halogen atoms by reacting a polyhalophenol and a carbonate precursor in the presence of a catalyst selected from the group consisting of trimethyl amine, triethyl amine, tripropyl amine, tributyl amine, methyl ethyl amine, dimethyl ethyl amine, quinoline, isoquinoline, tetramethyl ammonium chloride, trimethyl ammonium propyl iodide, benzyl trimethyl ammonium iodide, n-butyl-triphenyl phosphonium bromide, methyl-triphenyl phosphonium bromide, and mixtures thereof, in a basic aqueous medium, the improvement comprising carrying out the reaction in a continuous, single stage at a pH in the range of about 10.5 to 11.5 and in the presence of a chlorinated hydrocarbon solvent in which the polyhalodiphenyl carbonate is essentially insoluble and in which color bodies associated with the polyhalophenol starting material are soluble and retained.

3. The method of claim 1 wherein the solvent is methylene chloride.

4. The method of claim 1 wherein the pH is maintained by the addition as necessary to the reaction of a base chosen from the group consisting of alkali metal hydroxide and alkaline earth metal hydroxide.

5. The method of claim 4 wherein the base is sodium hydroxide.

* * * * *